(12) United States Patent
Sheppard et al.

(10) Patent No.: US 6,498,235 B2
(45) Date of Patent: Dec. 24, 2002

(54) TESTIS SPECIFIC GLYCOPROTEIN ZPEP10

(75) Inventors: Paul O. Sheppard, Redmond, WA (US); Christopher S. Piddington, Thousand Oaks, CA (US); Jeff L. Ellsworth, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 40 days.

(21) Appl. No.: 09/789,453

(22) Filed: Feb. 20, 2001

(65) Prior Publication Data

US 2002/0102704 A1 Aug. 1, 2002

Related U.S. Application Data

(62) Division of application No. 09/441,346, filed on Nov. 16, 1999, now Pat. No. 6,242,588.
(60) Provisional application No. 60/109,216, filed on Nov. 20, 1998.

(51) Int. Cl.[7] .......................... C07K 1/00; C07K 14/00; C07K 17/08; C07K 2/00; A61K 38/00
(52) U.S. Cl. ...................... 530/350; 530/300; 530/324; 514/1; 514/2; 514/4
(58) Field of Search ................................ 530/300, 324, 530/350; 514/1, 2, 4

(56) References Cited

PUBLICATIONS

U.S. patent application Ser. No. 09/441,346, Sheppard et al., filed Nov. 16, 1999.
Wilson, WashU–Merck EST Project, 1997, GenBank ACC#AA459848.
Strausberg, NCI, Cancer Genome Anatomy Project, 1998, GenBank Acc#AA868533.
Lexicon Pharmaceuticals, Mouse OST, 1998, OST16697.
Lexicon Pharmaceuticals, Mouse OST, 1998, OST16698.

Primary Examiner—Yvonne Eyler
Assistant Examiner—Alana M. Harris
(74) Attorney, Agent, or Firm—Brian J. Walsh

(57) ABSTRACT

The present invention relates to zpep10 polypeptides and polynucleotides encoding the same. Zpep10 polypeptide is a testis-specific membrane glycoprotein. Zpep10 polypeptides would be useful for modulating spermatogenesis and egg-sperm interaction and would be useful to study or modulate these functions in in vitro or in vivo systems. The present invention also includes antibodies to the zpep10 polypeptides.

13 Claims, 3 Drawing Sheets

```
101   0.17                                            F ===
102   0.28                                            P ===
103  -0.28                                      === G
104   0.22                                            S ==
105   0.08                                            Q =
106   0.55                                            D ======
107  -0.25                                   == L
108  -0.25                                  === W
109   0.02                                            E
110  -0.78                          ======= A
111  -1.27                    =========== K
112  -2.07           ================ I
113  -2.18          ================= L
114  -2.45         ================== L
115  -2.23          ================= L
116  -2.35         ================== s
117  -2.08            =============== I
118  -2.08            =============== F
119  -1.97             ============== g
120  -1.97             ============== A
121  -2.13            =============== F
122  -2.02            =============== L
123  -2.28          ================= L
124  -2.28          ================= L
125  -2.28          ================= g
126  -1.97             ============== V
127  -1.22                    =========== L
128  -0.87                        ======== s
129   0.02                                            L
130   0.23                                            L ==
131   0.23                                            V ==
132   0.63                                            E ======
133   0.16                                            S ==
134   0.72                                            h =======
135   0.56                                            H =====
136   0.76                                            L ========
137   0.87                                            Q =========
138   0.00                                            A
139   0.00                                            K
140   0.00                                            S
141   0.00                                            G
142   0.00                                            L
  ;         |---------|---------|---------|---------|---------|---------|
  ;        -3        -2        -1         0         1         2         3
         Hydrophobic                                            Hydrophilic ;
```

Fig. 1C

SEQUENCE LISTING

<160> NUMBER OF SEQ ID NOS: 14

<210> SEQ ID NO 1
<211> LENGTH: 1094
<212> TYPE: DNA
<213> ORGANISM: Homo sapiens
<220> FEATURE:
<221> NAME/KEY: CDS
<222> LOCATION: (79)...(504)

<400> SEQUENCE: 1

```
ggcaagggct ggagccaggg ctgcagagca ttccttggct cagctggggc agcgccgccc       60
catcccccag tggtcctc atg tgg agg ctg gca cta ggc ggg gtt ttc ctg      111
                    Met Trp Arg Leu Ala Leu Gly Gly Val Phe Leu
                     1               5                      10 gca gcc gcc cag gct tgt gtc ttc tgt cgc ctc cca gcc cac gac ttg      159
Ala Ala Ala Gln Ala Cys Val Phe Cys Arg Leu Pro Ala His Asp Leu
                15                  20                  25 tca ggc cgc ctg gct cgg ctc tgc agc cag atg gag gcc agg cag aag      207
Ser Gly Arg Leu Ala Arg Leu Cys Ser Gln Met Glu Ala Arg Gln Lys
            30                  35                  40 gaa tgt ggg gcc tcc cca gac ttc tcg gcc ttt gcc tta gat gag gtg      255
Glu Cys Gly Ala Ser Pro Asp Phe Ser Ala Phe Ala Leu Asp Glu Val
        45                  50                  55 tcc atg aac aaa gtc aca gag aag act cac aga gtc ctg agg gtc atg      303
Ser Met Asn Lys Val Thr Glu Lys Thr His Arg Val Leu Arg Val Met
 60                  65                  70                  75 ggg ggc agc acc acg ctg tac aac tgc tcc acc tgc aag ggg acg gag      351
```

```
Gly Gly Ser Thr Thr Leu Tyr Asn Cys Ser Thr Cys Lys Gly Thr Glu
                80                  85                  90 gtg tcc tgc tgg ccc cga aag cgc tgc ttc cca gga agt cag gat ctt      399
Val Ser Cys Trp Pro Arg Lys Arg Cys Phe Pro Gly Ser Gln Asp Leu
            95                 100                 105 tgg gaa gcc aag att ctg ctc ctc tcc atc ttc gga gct ttc ctg ctt      447
Trp Glu Ala Lys Ile Leu Leu Leu Ser Ile Phe Gly Ala Phe Leu Leu
        110                 115                 120 ctg ggt gtt ctg agc ctc ctg gtg gag tcc cac cac ctc caa gca aaa      495
Leu Gly Val Leu Ser Leu Leu Val Glu Ser His His Leu Gln Ala Lys
    125                 130                 135 agt ggc ttg tgaagacgct gaaaacctcc cagcctccag ctctaagggg              544
Ser Gly Leu
140 tatgcactca aacttccac atcccttgga ggggaaccag tcagcccctt agtcccagct      604 ccaaagacag tctccagacc ctaaaaccca gacatccctg cttctggttg gtgagataat    664 gaaaaacaag aaaatcccca aaacccaga tcccccacaa tcccagtgtc agatggcctc     724 ccgggaaccc aggcacccac agctggaaag ttcctcccct ccagcccctca accaatcaca   784 tggctgtcaa caatgccagg aaaatatcta cagaaggaaa gaatcccta cgccactccc    844 accacaccca cacccccttc tgcctgttcc gggaaagcgg gggcatctgc cccagaagct   904 attccaggcc tcctatgac tgatggggaa tccgggaatg catgttctgg aaaactcacc    964 ccactagagt gagatcacat cagtgggttc gcgggcatgc cctccctcca tcgtgttaac  1024 agtttgaaat cctggcctcc ctcagaggcc tccatcctgc caggcctaag taaaacttgc  1084 tgttcatgga                                                         1094

<210> SEQ ID NO 2
<211> LENGTH: 142
<212> TYPE: PRT
<213> ORGANISM: Homo sapiens

<400> SEQUENCE: 2

Met Trp Arg Leu Ala Leu Gly Gly Val Phe Leu Ala Ala Ala Gln Ala
1               5                   10                  15

Cys Val Phe Cys Arg Leu Pro Ala His Asp Leu Ser Gly Arg Leu Ala
            20                  25                  30

Arg Leu Cys Ser Gln Met Glu Ala Arg Gln Lys Glu Cys Gly Ala Ser
        35                  40                  45

Pro Asp Phe Ser Ala Phe Ala Leu Asp Glu Val Ser Met Asn Lys Val
    50                  55                  60

Thr Glu Lys Thr His Arg Val Leu Arg Val Met Gly Gly Ser Thr Thr
65                  70                  75                  80

Leu Tyr Asn Cys Ser Thr Cys Lys Gly Thr Glu Val Ser Cys Trp Pro
                85                  90                  95

Arg Lys Arg Cys Phe Pro Gly Ser Gln Asp Leu Trp Glu Ala Lys Ile
            100                 105                 110

Leu Leu Leu Ser Ile Phe Gly Ala Phe Leu Leu Gly Val Leu Ser
        115                 120                 125

Leu Leu Val Glu Ser His His Leu Gln Ala Lys Ser Gly Leu
    130                 135                 140

<210> SEQ ID NO 3
<211> LENGTH: 426
<212> TYPE: DNA
<213> ORGANISM: Artificial Sequence
```

```
<220> FEATURE:
<223> OTHER INFORMATION: Degenerate nucleotide sequence encoding the
      zpep10 polypeptide of SEQ ID NO:2
<221> NAME/KEY: variation
<222> LOCATION: (1)...(426)
<223> OTHER INFORMATION: Each N is independently any nucleotide.

<400> SEQUENCE: 3
atgtggmgny tngcnytngg nggngtntty ytngcngcng cncargcntg ygtnttytgy     60
mgnytnccng cncaygayyt nwsnggnmgn ytngcnmgny tntgywsnca ratggargcn    120
mgncaraarg artgyggngc nwsnccngay ttywsngcnt tygcnytnga ygargtnwsn    180
atgaayaarg tnacngaraa racncaymgn gtnytnmgng tnatggnggg nwsnacnacn    240
ytntayaayt gywsnacntg yaarggnacn gargtnwsnt gytggccnmg naarmgntgy    300
ttyccnggnw sncargayyt ntgggargcn aarathytny tnytnwsnat httyggngcn    360
ttyytnytny tnggngtnyt nwsnytnytn gtngarwsnc aycayytnca rgcnaarwsn    420 ggnytn                                                              426

<210> SEQ ID NO 4
<211> LENGTH: 17
<212> TYPE: DNA
<213> ORGANISM: Artificial Sequence
<220> FEATURE:
<223> OTHER INFORMATION: Degenerate oligonucleotide probe
<221> NAME/KEY: variation
<222> LOCATION: (1)...(17)
<223> OTHER INFORMATION: Each N is independently any nucleotide

<400> SEQUENCE: 4
cargcntgyg tnttytg                                                   17

<210> SEQ ID NO 5
<211> LENGTH: 17
<212> TYPE: DNA
<213> ORGANISM: Artificial Sequence
<220> FEATURE:
<223> OTHER INFORMATION: Degenerate oligonucleotide probe
<221> NAME/KEY: variation
<222> LOCATION: (1)...(17)
<223> OTHER INFORMATION: Each N is independently any nucleotide.

<400> SEQUENCE: 5
caraargart gyggngc                                                   17

<210> SEQ ID NO 6
<211> LENGTH: 17
<212> TYPE: DNA
<213> ORGANISM: Artificial Sequence
<220> FEATURE:
<223> OTHER INFORMATION: Degenerate oligonucleotide probe
<221> NAME/KEY: variation
<222> LOCATION: (1)...(17)
<223> OTHER INFORMATION: Each N is independently any nucleotide.

<400> SEQUENCE: 6
atgaayaarg rnacnga                                                   17

<210> SEQ ID NO 7
<211> LENGTH: 17
<212> TYPE: DNA
<213> ORGANISM: Artificial Sequence
<220> FEATURE:
<223> OTHER INFORMATION: Degenerate oligonucleotide probe
<221> NAME/KEY: variation
<222> LOCATION: (1)...(17)
```

<223> OTHER INFORMATION: Each N is independently any nucleotide.

<400> SEQUENCE: 7
grnacngara aracnca                                                     17

<210> SEQ ID NO 8
<211> LENGTH: 17
<212> TYPE: DNA
<213> ORGANISM: Artificial Sequence
<220> FEATURE:
<223> OTHER INFORMATION: Degenerate oligonucleotide probe
<221> NAME/KEY: variation
<222> LOCATION: (1)...(17)
<223> OTHER INFORMATION: Each N is independently any nucleotide.

<400> SEQUENCE: 8
acntgyaarg gnacnga                                                     17

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide ZC16,186

<400> SEQUENCE: 9
atcagtcata ggagggcctg gaata                                            25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide ZC16,187

<400> SEQUENCE: 10
tccctgcttc tggttggtga gataa                                            25

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide ZC 13,006

<400> SEQUENCE: 11
ggctgtcctc taagcgtcac                                                  20

<210> SEQ ID NO 12
<211> LENGTH: 12
<212> TYPE: DNA
<213> ORGANISM: Artificial Sequence
<220> FEATURE:
<223> OTHER INFORMATION: Nucleotide contig example

<400> SEQUENCE: 12
atggcttagc tt                                                          12

<210> SEQ ID NO 13
<211> LENGTH: 12
<212> TYPE: DNA
<213> ORGANISM: Artificial Sequence
<220> FEATURE:
<223> OTHER INFORMATION: Nucleotide contig example

<400> SEQUENCE: 13

-continued

```
tagcttgagt ct                                                    12

<210> SEQ ID NO 14
<211> LENGTH: 12
<212> TYPE: DNA
<213> ORGANISM: Artificial Sequence
<220> FEATURE:
<223> OTHER INFORMATION: Nucleotide contig example

<400> SEQUENCE: 14
gtcgactacc ga                                                    12
```

TESTIS SPECIFIC GLYCOPROTEIN ZPEP10

REFERENCE TO RELATED APPLICATIONS

This application is a divisional of application Ser. No. 09/441,346 filed Nov. 16, 1999 now issued as U.S. Pat. No. 6,242,588 which is related to Provisional Application No. 60/109,216, filed on Nov. 20, 1998. Under 35 U.S.C. § 119(e)(1), this application claims benefit of said Provisional Application.

BACKGROUND OF THE INVENTION

The testis is the center for spermatogenesis, the process by which a germ cell proceeds through multiple stages of differentiation, and culminates in the formation of a terminally differentiated cell (spermatozoa or sperm) having a unique function. Within the testis are seminiferous tubules, where spermatogonium mature into spermatozoa. Surrounding the seminiferous tubules are interstitial cells which secrete androgens, such as testosterone, required for maturation and function of the testis and development of secondary sexual characteristics. Disorders of the testis are common and have profound effect. Infertility can result from disorders occurring during spermatogenesis. Many developmental disorders, such as hypogonadism, are associated with altered sex hormone production and levels in the testis. Testicular cancer, although rare, is the most common form of cancer in young men between the ages of 15 and 35.

Testis specific proteins have therapeutic value in the treatment of disorders associated with the testis such as dysfunctional sperm production, infertility and testicular cancer. Towards this end, the present invention provides novel testis-specific membrane glycoproteins, soluble ligands, agonists and antagonists, related compositions and methods as well as other uses that should be apparent to those skilled in the art from the teachings herein.

BRIEF DESCRIPTION OF THE DRAWING

Figure 1B:
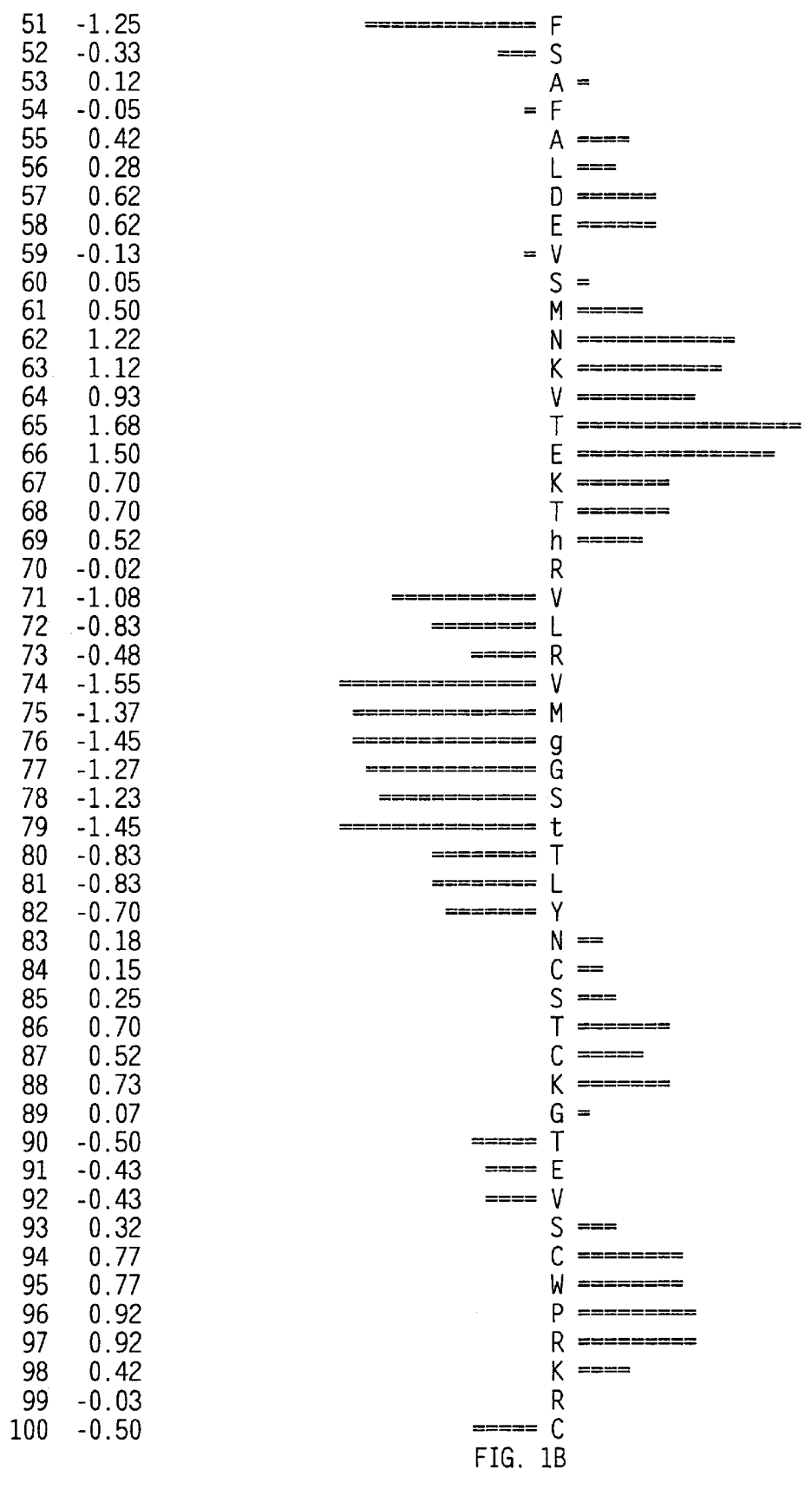

FIGS. 1A–K are a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the FIG. by lower case letters.

DETAILED DESCRIPTION OF THE INVENTION

Figure 1A:
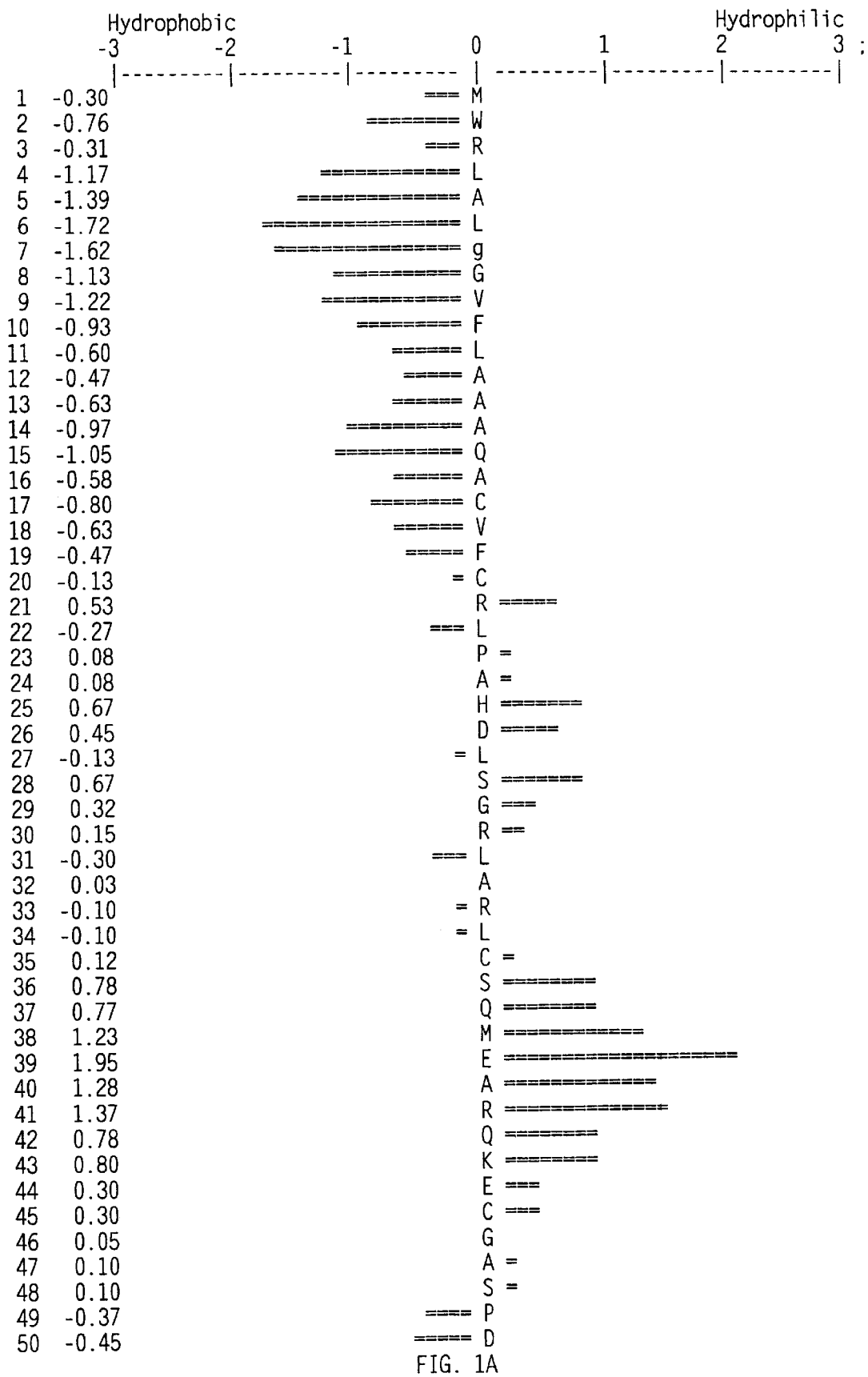

Prior to setting forth the invention in detail, it may be helpful to the understanding thereof to define the following terms:

The term "affinity tag" is used herein to denote a peptide segment that can be attached to a polypeptide to provide for purification or detection of the polypeptide or provide sites for attachment of the polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988; available from Eastman Kodak Co., New Haven, Conn.), streptavidin binding peptide, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' (SEQ ID NO:12) are 5'-TAGCTTgagtct-3' (SEQ ID NO: 13) and 3'-gtcgacTACCGA-5' (SEQ ID NO: 14).

The term "degenerate nucleotide sequence" denotes a sequence of nucleotides that includes one or more degenerate codons (as compared to a reference polynucleotide molecule that encodes a polypeptide) Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" denotes a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "soluble receptor" is used herein to refer to a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

Within one aspect the invention provides an isolated polypeptide comprising an extracellular domain, wherein the extracellular domain comprises amino acid residues 22 to 111 of the amino acid sequence of SEQ ID NO:2. Within one embodiment polypeptide further comprises a transmembrane domain that resides in a carboxyl-terminal position relative to the extracellular domain, wherein the transmembrane domain comprises amino acid residues 112 to 133 of the amino acid sequence of SEQ ID NO:2. Within another embodiment the polypeptide further comprises a cytoplasmic domain that resides in a carboxyl-terminal position relative to the transmembrane domain, wherein the cytoplasmic domain comprises amino acid residues 134 to 142 of the amino acid sequence of SEQ ID NO:2. Within another embodiment the polypeptide further comprises a secretory signal that resides in an amino-terminal position relative to the extracellular domain, wherein the secretory signal sequence comprises amino acid residues 1 to 20 of the amino acid sequence of SEQ ID NO:2.

The invention also provides an isolated polypeptide as described herein comprising amino acid residue 1 to amino acid residue 142 of SEQ ID NO:2.

Also provided is an isolated polypeptide as described herein, covalently linked amino terminally or carboxy terminally to a moiety selected from the group consisting of affinity tags, toxins, radionucleotides, enzymes and fluorophores.

Within another aspect the invention provides an isolated polypeptide comprising a sequence of amino acid residues that is at least 80% identical to a amino acid residue 21 to amino acid residue 142 of SEQ ID NO:2, wherein the polypeptide specifically binds with an antibody that specifically binds with a polypeptide having the amino acid sequence of SEQ ID NO:2. Within one embodiment any difference between the amino acid sequence of the isolated polypeptide and the corresponding amino acid sequence of SEQ ID NO:2 is due to a conservative amino acid substitution. Within another embodiment the amino acid percent identity is determined using a FASTA program with ktup=1, gap opening penalty=10, gap extension penalty=1, and substitution matrix=blosum62, with other parameters set as default.

The invention provides an isolated polypeptide comprising the amino acid sequence of amino acid residue 1 to amino acid residue 20 of SEQ ID NO:2.

Also provided is an isolated polypeptide selected from the group consisting of:

a) amino acid residues 21–111 of SEQ ID NO:2;
b) amino acid residues 112–133 of SEQ ID NO:2;
c) amino acid residues 134–142 of SEQ ID NO:2;
d) amino acid residues 1–20 of SEQ ID NO:2;
e) amino acid residues 21–133 of SEQ ID NO:2;
f) amino acid residues 112–142 of SEQ ID NO:2;
g) amino acid residues 1–111 of SEQ ID NO:2; and
h) amino acid residues 1–133 of SEQ ID NO:2.

Within another aspect the invention provides a fusion protein consisting of a first portion and a second portion joined by a peptide bond, the first portion comprising a polypeptide as described herein, and the second portion comprising another polypeptide.

The invention also provides a polypeptide as described herein in combination with a pharmaceutically acceptable vehicle.

Within another aspect the invention provides an antibody that specifically binds to an epitope of a polypeptide of as described herein. Within one embodiment the antibody is selected from the group consisting of: a) polyclonal antibody; b) murine monoclonal antibody; c) humanized antibody derived from b); and d) human monoclonal antibody.

Within another embodiment the antibody fragment is selected from the group consisting of F(ab'), F(ab), Fab', Fab, Fv, scFv, and minimal recognition unit.

Also provides is an anti-idiotype antibody that specifically binds to an antibody as described herein. Also provided is a binding protein that specifically binds to an epitope of a polypeptide as described herein.

Within another aspect the invention provides a method of producing an antibody to a polypeptide comprising: inoculating an animal with a polypeptide as described herein; wherein the polypeptide elicits an immune response in the animal to produce the antibody; and isolating the antibody from the animal.

Within another aspect is provided an isolated polynucleotide encoding a polypeptide comprising an extracellular domain, wherein the extracellular domain comprises amino acid residues 22 to 111 of the amino acid sequence of SEQ ID NO:2. Within one embodiment the polypeptide further comprises a transmembrane domain that resides in a carboxyl-terminal position relative to the extracellular domain, wherein the transmembrane domain comprises amino acid residues 112 to 133 of the amino acid sequence of SEQ ID NO.2. Within another embodiment the polypeptide further comprises a cytoplasmic domain that resides in a carboxyl-terminal position relative to the transmembrane domain, wherein the cytoplasmic domain comprises amino acid residues 134 to 142 of the amino acid sequence of SEQ ID NO:2. Within yet another embodiment the polypeptide further comprises a secretory signal that resides in an amino-terminal position relative to the extracellular domain, wherein the secretory signal sequence comprises amino acid residues 1 to 20 of the amino acid sequence of SEQ ID NO:2.

The invention also provides an isolated polynucleotide as described herein encoding a polypeptide comprising amino acid residue 1 to amino acid residue 142 of SEQ ID NO:2.

Also provided is an isolated polynucleotide as described herein, wherein the polypeptide is covalently linked amino terminally or carboxy terminally to a moiety selected from the group consisting of affinity tags, toxins, radionucleotides, enzymes and fluorophores.

Within another aspect the invention provides an isolated polynucleotide encoding a polypeptide comprising a sequence of amino acid residues that is at least 80% identical to a amino acid residue 21 to amino acid residue 142 of SEQ ID NO:2, wherein the polypeptide specifically binds with an antibody that specifically binds with a polypeptide having the amino acid sequence of SEQ ID NO:2. Within one embodiment any difference between the amino acid sequence of the isolated polypeptide and the corresponding amino acid sequence of SEQ ID NO:2 is due to a conservative amino acid substitution. Within another embodiment the amino acid percent identity is determined using a FASTA program with ktup=1, gap opening penalty=10, gap extension penalty=1, and substitution matrix=blosum62, with other parameters set as default.

The invention also provides an isolated polynucleotide selected from the group consisting of:

a) a sequence of nucleotides from nucleotide 139 to nucleotide 411 of SEQ ID NO:1;

b) a sequence of nucleotides from nucleotide 139 to nucleotide 477 of SEQ ID NO:1;

c) a sequence of nucleotides from nucleotide 139 to nucleotide 504 of SEQ ID NO:1;

d) a sequence of nucleotides from nucleotide 79 to nucleotide 504 of SEQ ID NO:1;

e) a sequence of nucleotides from nucleotide 1 to nucleotide 1094 of SEQ ID NO:1;

f) a polynucleotide that remains hybridized following stringent wash conditions to a polynucleotide consisting of the nucleotide sequence of SEQ ID NO:1, or the complement of SEQ ID NO:1; and g) nucleotide sequences complementary to a), b), c), d), e), or f.

Further provided is an isolated polynucleotide encoding a fusion protein consisting of a first portion and a second portion joined by a peptide bond, the first portion comprises a polypeptide as described herein; and the second portion comprising another polypeptide.

Also provided is an isolated polynucleotide encoding a fusion protein comprising a secretory signal sequence having the amino acid sequence of amino acid residues 1–20 of SEQ ID NO:2, wherein the secretory signal sequence is operably linked to an additional polypeptide.

The invention also provides an isolated polynucleotide comprising the sequence of nucleotide 1 to nucleotide 426 of SEQ ID NO:3.

Within another aspect is provided an expression vector comprising the following operably linked elements:

a transcription promoter; a DNA segment encoding a polypeptide as described herein; and a transcription terminator.

Within one embodiment the DNA segment encodes a polypeptide covalently linked amino terminally or carboxy terminally to an affinity tag. Within another embodiment the DNA segment further encodes a secretory signal sequence operably linked to the polypeptide. Within yet another embodiment the secretory signal sequence comprises residues 1 to 20 of SEQ ID NO:2.

The invention also provides a cultured cell into which has been introduced an expression vector as described herein; wherein the cell expresses the polypeptide encoded by the DNA segment.

The invention also provides a method of producing a polypeptide comprising: culturing a cell into which has been introduced an expression vector as described herein; whereby the cell expresses the polypeptide encoded by the DNA segment; and recovering the expressed polypeptide.

The present invention is based in part upon the discovery of a novel DNA sequence (SEQ ID NO:1) and the corresponding deduced polypeptide sequence (SEQ ID NO:2) which encode a testis-specific polypeptide designated zpep10. The novel zpep10 polypeptide-encoding polynucleotides of the present invention were initially identified by querying an EST database for polypeptides containing repetitive patterns and post-translational processing sites yielding potentially active peptides. The polypeptide corresponding to an EST meeting those search criteria was further analyzed and found to be a membrane glycoprotein. The EST sequence was from a testis cell library. Several clones considered likely to contain the entire coding region were used for sequencing and resulted in an incompletely spliced message. A minimal nucleotide sequence having all potential introns spliced out was generated. The full length cDNA sequence was identified from a testis library and is disclosed in SEQ ID NO:1. The deduced amino acid sequence of this polynucleotide sequence is disclosed in SEQ ID NO:2. Analysis of the DNA encoding a zpep10 polypeptide (SEQ ID NO:1) revealed an open reading frame encoding 142 amino acids (SEQ ID NO:2) comprising a putative signal sequence (residues 1 to 20 of SEQ ID NO:2, nucleotides 79 to 138 of SEQ ID NO:1) and 122 amino acids of predicted mature sequence (residues 21 to 142 of SEQ ID NO:2, nucleotides 139 to 504 of SEQ ID NO:1) containing an extracellular domain (residues 21 to 111 of SEQ ID NO:2, nucleotides 139 to 411 of SEQ ID NO:1) containing six cysteine residues, amino acid residues 35, 45, 84, 87, 94 and 100 of SEQ ID NO:2, a tri-basic amino acid cleavage site, amino acid residues 97–99 of SEQ ID NO:2; potential N-linked glycosylation sites at amino acid residues 83 and 86 of SEQ ID NO:2; and potential O-glycosylation sites at amino acid residues 28, 36, 48, 52, 60, 65, 68, 78, 79, 80, 85, 86, 90, 93 and 104 of SEQ ID NO:2; a putative transmembrane domain (residues 112 to 133 of SEQ ID NO:2, nucleotides 412 to 477 of SEQ ID NO:1) and a cytoplasmic domain (residues 134 to 142 of SEQ ID NO:2, nucleotides 478 to 504 of SEQ ID NO:1). The overall structure of zpep10 is helical. Those skilled in the art will recognize that these domain boundaries are approximate, and are based on alignments with known proteins and predictions of protein folding. Zpep10 does not share significant homology with any known protein.

Many proteins and hormones are processed into their mature forms by highly-specific proteolytic enzymes, prohormone convertases, which carry out intracellular cleavage at the COOH-terminal side of dibasic sites within their substrate polypeptides. There are only a few dibasic amino acid combinations, including lys-lys, arg-arg, arg-lys and lys-arg. Zpep10 polypeptides may be processed into an active form through cleavage after lys (amino acid residue 98 of SEQ ID NO:2) or arg (amino acid residue 99 of SEQ ID NO:2) of the tribasic site arg-lys-arg (amino acid residues 97–99 of SEQ ID NO:2). Prohormone convertase PC4 exhibits highly specific testis expression (WIPO publication, WO98/50560) and may serve to cleave the zpep10 polypeptide.

The present invention therefore provides post-translationally modified polypeptides or polypeptide fragments having the amino acid sequence from amino acid residue 21 to amino acid residue 98 of SEQ ID NO:2 and the amino acid sequence from amino acid residue 21 to amino acid residue 99 of SEQ ID NO:2. Examples of post translational modifications include proteolytic cleavage, glycosylation and disulfide bonding.

Analysis of the tissue distribution of the mRNA corresponding to this novel DNA by Northern blot and Dot blot analysis suggest that zpep10 is a testis-specific protein having a transcript of about 1.5 kb.

The present invention further provides polynucleotide molecules, including DNA and RNA molecules, encoding zpep10 proteins. The polynucleotides of the present invention include the sense strand; the anti-sense strand; and the DNA as double-stranded, having both the sense and antisense strand annealed together by their respective hydrogen bonds. Representative DNA sequences encoding zpep10 proteins are set forth in SEQ ID NO:1. DNA sequences encoding other zpep10 proteins can be readily generated by those of ordinary skill in the art based on the genetic code. Counterpart RNA sequences can be generated by substitution of U for T.

Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zpep10polypeptide of SEQ ID NO:2. Those skilled in the art will recognize that the degenerate sequence of SEQ ID NO:3 also provides all RNA sequences encoding SEQ ID NO:2 by substituting U for T. Thus, zpep10 polypeptide-encoding polynucleotides comprising nucleotide 1 to nucleotide 426 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Nucleotide |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | | | | | | Degenerate Codon |
|---|---|---|---|---|---|---|---|---|
| Cys | C | TGC | TGT | | | | | TGY |
| Ser | S | AGC | AGT | TCA | TCC | TCG | TCT | WSN |
| Thr | T | ACA | ACC | ACG | ACT | | | ACN |
| Pro | P | CCA | CCC | CCG | CCT | | | CCN |
| Ala | A | GCA | GCC | GCG | GCT | | | GCN |
| Gly | G | GGA | GGC | GGG | GGT | | | GGN |
| Asn | N | AAC | AAT | | | | | AAY |
| Asp | D | GAC | GAT | | | | | GAY |
| Glu | E | GAA | GAG | | | | | GAR |
| Gln | Q | CAA | CAG | | | | | CAR |
| His | H | CAC | CAT | | | | | CAY |
| Arg | R | AGA | AGG | CGA | CGC | CGG | CGT | MGN |
| Lys | K | AAA | AAG | | | | | AAR |
| Met | M | ATG | | | | | | ATG |
| Ile | I | ATA | ATC | ATT | | | | ATH |
| Leu | L | CTA | CTC | CTG | CTT | TTA | TTG | YTN |
| Val | V | GTA | GTC | GTG | GTT | | | GTN |
| Phe | F | TTC | TTT | | | | | TTY |
| Tyr | Y | TAC | TAT | | | | | TAY |
| Trp | W | TGG | | | | | | TGG |
| Ter | — | TAA | TAG | TGA | | | | TRR |
| Asn\|Asp | B | | | | | | | RAY |
| Glu\|Gln | Z | | | | | | | SAR |
| Any | X | | | | | | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, other polynucleotide probes, primers, fragments and sequences recited herein or sequences complementary thereto. Polynucleotide hybridization is well known in the art and widely used for many applications, see for example, Sambrook et al., *Molecular Cloning: A Laboratory Manual, Second Edition*, Cold Spring Harbor, N.Y., 1989; Ausubel et al., eds., *Current Protocols in Molecular Biology*, John Wiley and Sons, Inc., NY, 1987; Berger and Kimmel, eds., Guide to Molecular Cloning Techniques, *Methods in Enzymology*, volume 152, 1987 and Wetmur, *Crit. Rev. Biochem. Mol. Biol.* 26:227–59, 1990. Polynucleotide hybridization exploits the ability of single stranded complementary sequences to form a double helix hybrid. Such hybrids include DNA-DNA, RNA-RNA and DNA-RNA.

Hybridization will occur between sequences which contain some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the thermal melting point ($T_m$) of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing up to 6× SSC and 0–50% formamide. A higher degree of stringency can be achieved at temperatures of from 40–70° C. with a hybridization buffer having up to 4× SSC and from 0–50% formamide. Highly stringent conditions typically encompass temperatures of 42–70° C. with a hybridization buffer having up to 1× SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, see for example (Sambrook et al., ibid.; Ausubel et al., ibid.; Berger and Kimmel, ibid. and Wetmur, ibid.) and are specific for DNA, RNA and DNA-RNA hybrids and polynucleotide probe sequences of varying length. Sequence analysis software such as Oligo 4.0 (publicly available shareware) and Primer Premier (PREMIER Biosoft International, Palo Alto, Calif.) as well as sites on the Internet, are available tools for analyzing a given sequence and calculating $T_m$ based on user defined criteria. Such programs can also analyze a given sequence under defined conditions and suggest suitable probe sequences. Typically, hybridization of longer polynucleotide sequences, >50 bp, is done at temperatures of about 20–25° C. below the calculated $T_m$. For smaller probes, <50 bp, hybridization is typically carried out at the $T_m$ or 5–10° C. below. This allows for the maximum rate of hybridization for DNA-DNA and DNA-RNA hybrids.

The length of the polynucleotide sequence influences the rate and stability of hybrid formation. Smaller probe sequences, <50 bp, come to equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing NaCl. Therefor, the higher the G-C content, the more stable the hybrid. Even distribution of G and C residues within the sequence also contribute positively to hybrid stability. Base pair composition can be manipulated to alter the $T_m$ of a given sequence, for example, 5-methyldeoxycytidine can be substituted for deoxycytmidine and 5-bromodeoxuride can be substituted for thymidine to increase the $T_m$. 7-deazz-2'-deoxyguanosine can be substituted for guanosine to reduce dependence on $T_m$.

Ionic concentration of the hybridization buffer also effects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1× SSC: 0.15 M NaCl, 15 mM sodium citrate) or SSPE (1× SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM-1 M $Na^+$. Premixed hybridization solutions are also available from commercial sources such as Clontech Laboratories (Palo Alto, Calif.) and Promega Corporation (Madison, Wis.) for use according to manufacturer's instruction. Addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As previously noted, the isolated zpep10polynucleotides of the present invention include DNA and RNA. Methods for isolating DNA and RNA are well known in the art. It is generally preferred to isolate RNA from lymph node, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)+ RNA is prepared from total RNA using the method of Aviv and Leder (*Proc. Natl. Acad. Sci. USA* 69:1408–12, 1972). Complementary DNA (cDNA) is prepared from poly(A)+ RNA using known methods. Polynucleotides encoding zpep10polypeptides are then identified and isolated by, for example, hybridization or PCR.

The polynucleotides of the present invention can also be synthesized using automated equipment. The current method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. Gene synthesis methods are well known in the art. See, for example, Glick and Pasternak, *Molecular Biotechnology, Principles & Applications of Recombinant DNA*, ASM Press, Washington, D.C., 1994; Itakura et al., *Annu. Rev. Biochem.* 53: 323–356, 1984; and Climie et al., *Proc. Natl. Acad. Sci. USA* 87:633–637, 1990.

The zpep10 polynucleotide sequences disclosed herein can be used to isolate polynucleotides encoding other zpep10 proteins. Such other proteins include alternatively spliced cDNAs (including cDNAs encoding secreted zpep10 proteins) and counterpart polynucleotides from other species (orthologs). These orthologous polynucleotides can be used, inter alia, to prepare the respective orthologous proteins. Other species of interest include, but are not limited to, mammalian, avian, amphibian, reptile, fish, insect and other vertebrate and invertebrate species. Of particular interest are zpep10 polynucleotides and proteins from other mammalian species, including human and other primates, porcine, ovine, bovine, canine, feline, and equine polynucleotides and proteins. Orthologs of mouse zpep10, for example, can be cloned using information and compositions provided by the present invention in combination with conventional cloning techniques. For example, a cDNA can be cloned using mRNA obtained from a tissue or cell type that expresses zpep10 as disclosed herein. Suitable sources of mRNA can be identified by probing Northern blots with probes designed from the sequences disclosed herein. A library is then prepared from mRNA of a positive tissue or cell line. A zpep10-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zpep10 sequence disclosed herein. Within an additional method, the cDNA library can be used to transform or transfect host cells, and expression of the cDNA of interest can be detected with an antibody to zpep10 polypeptide. Similar techniques can also be applied to the isolation of genomic clones. Electronic databases can also be screened for EST sequences of zpep10 orthologs. Degenerate polynucleotide primer sequences useful for identifying zpep10 orthologs would include:

```
zpep10 residues 15-20 of SEQ ID NO:2
        CARGCNTGYGTNTTYTG  (SEQ ID NO:4)
zpep10 residues 42-47 of SEQ ID NO:2
        CARAARGARTGYGGNGC  (SEQ ID NO:5)
zpep10 residues 61-66 of SEQ ID NO:2
        ATGAAYAARGRNACNGA  (SEQ ID NO:6)
zpep10 residues 64-69 of SEQ ID NO:2
        GRNACNGARAARACNCA  (SEQ ID NO:7)
zpep10 residues 86-91 of SEQ ID NO:2
        ACNTGYAARGGNACNGA  (SEQ ID NO:8).
```

Those skilled in the art will recognize that the sequences disclosed in SEQ ID NO:1 and SEQ ID NO:2 represent a single allele of the human zpep10 gene and polypeptide, and that allelic variation and alternative splicing are expected to occur. In addition, allelic variants can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zpep10 polypeptide are included within the scope of the present invention, as are polypeptides encoded by such cDNAs and mRNAs. Allelic variants and splice variants of these sequences can be cloned by probing cDNA or. genomic libraries from different individuals or tissues according to standard procedures known in the art.

The present invention also provides isolated zpep10 polypeptides that are substantially homologous to the polypeptide of SEQ ID NO:2 and its species orthologs. The term "substantially homologous" is used herein to denote polypeptides having 60%, preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs. Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |

TABLE 3-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zpep10. The FASTA algorithm is described by Pearson and Lipman, *Proc. Nat. Acad. Sci. USA* 85:2444, 1988, and by Pearson, *Meth. Enzymol.* 183:63, 1990.

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then re-scored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Natl. Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than -1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues or an affinity tag. Polypeptides comprising affinity tags can further comprise a proteolytic cleavage site between the zpep10 polypeptide and the affinity tag. Preferred such sites include thrombin cleavage sites and factor Xa cleavage sites.

TABLE 4

Conservative amino acid substitutions

| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homo-glutamine, pipecolic acid, thiazolidine carboxylic acid, dehydroproline, 3- and 4-methylproline, 3,3-dimethyl-proline, tert-leucine, norvaline, 2-azaphenyl-alanine, 3-azaphenylalanine, 4-azaphenylalanine, and 4-fluorophenyl-alanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:39–403, 1993).

A limited number of non-conservative amino acids, amino acids that are not encoded by the genetic code, non-naturally occurring amino acids, and unnatural amino acids may be substituted for zpep10 amino acid residues.

Essential amino acids in the zpep10 polypeptides of the present invention can be identified according to procedures known in the art, such as site-directed mutagenesis or alanine-scanning mutagenesis (Cunningham and Wells, *Science* 244: 1081–5, 1989). In the latter technique, single alanine mutations are introduced at every residue in the molecule, and the resultant mutant molecules are tested for biological activity (e.g., adhesion-modulation, differentiation-modulation or the like) to identify amino acid residues that are critical to the activity of the molecule. See also, Hilton et al., *J. Biol. Chem.* 271:4699–708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related proteins. Amino acid residues that might be considered essential in the zpep10 polypeptide are cysteine residues at amino acid residues 17, 20, 35, 45, 84, 87, 94 and 100 of SEQ ID NO:2; the potential arg-lys-arg tri-basic amino acid cleavage site at amino acid residues 97–99 of SEQ ID NO:2; the potential N-linked glycosylation sites at amino acid residues 83 and 86 of SEQ ID NO:2 and the potential O-glycosylation sites at amino acid residues 28, 36, 48, 52, 60, 65, 68, 78, 79, 80, 85, 86, 90, 93 and 104 of SEQ ID NO:2. A hydrophobicity profile of SEQ ID NO:2 is shown in the attached FIGURE. Those skilled in the art will recognize that this hydrophobicity will be taken into account when designing alterations in the amino acid sequence of a zpep10 polypeptide, so as not to disrupt the overall profile.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zpep10 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., ligand binding receptors) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to, for example, residues 21 to 111, 21 to 142 or 1 to 142 of SEQ ID NO:2 or allelic variants thereof and retain the properties of wild-type protein. Such polypeptides may include additional amino acids, such as affinity tags and the like. Such polypeptides may also include additional polypeptide segments as generally disclosed herein.

The invention also provides soluble polypeptides. It is preferred that these soluble polypeptides be extracellular polypeptides and be in a form substantially free of transmembrane and intracellular polypeptide segments. To direct the export of the soluble polypeptides from the host cell, the DNA encoding the soluble polypeptide is linked to a second DNA segment encoding a secretory peptide, such as a t-PA secretory peptide or the native zpep10 secretory signal sequence (amino acid residues 1–20 of SEQ ID NO:2). To facilitate purification of the secreted polypeptide, an N- or C-terminal extension, such as an affinity tag or another polypeptide or protein for which an antibody or other specific binding agent is available, can be fused to the soluble polypeptide.

The present invention also provides zpep10fusion proteins. For example, fusion proteins of the present invention encompass (1) a polypeptide selected from the following: a) a polypeptide comprising a sequence of amino acid residues from amino acid residue 21 to amino acid residue 111 of SEQ ID NO:2; and b) a polypeptide comprising a sequence of amino acid residues from amino acid residue 1 to amino acid residue 20 of SEQ ID NO:2; and (2) another polypeptide. The other polypeptide may be a signal peptide to facilitate secretion of the fusion protein, a transmembrane and/or cytoplasmic domain, or another soluble polypeptide or the like. For example, the extracellular portion of a zpep10 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zpep10 polypeptide fusions can be expressed in genetically engineered cells to produce a variety of multimeric zpep10 analogs. Auxiliary domains can be fused to zpep10 polypeptides to target them to specific cells, tissues, or macromolecules. For example, a soluble zpep10 polypeptide or protein could be targeted to a predetermined cell type by fusing a zpep10 polypeptide to a ligand that specifically binds to a receptor on the surface of the target cell. In this way, polypeptides and proteins can be targeted for therapeutic or diagnostic purposes. A zpep10 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The soluble zpep10 polypeptide is useful in studying the distribution of zpep10 receptors on tissues or specific cell lineages, and to provide insight into receptor/ligand biology. Using labeled soluble zpep10, cells expressing the ligand are identified by fluorescence immunocytometry or immunohistochemistry. The effects of zpep10 on steroidogenesis or Leydig or Sertoli cell expression can be examined by probing tissue slices with soluble zpep10 fusions, see for example, Daehlin et al., Scand. *J. Urol. Nephrol.* 19:7–12, 1985; Gavino et al., *Arch. Biochem. Biophys.* 233:741–7, 1984 and von Schnakenburg et al., *Acta Endocrinol.* 94:397–403, 1980). luteinizing hormone (LH) and follicle stimulating hormone (FSH) responses could also be examined in soluble zpep10-treated tissue slices.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al. (eds.), *Current Protocols in Molecular Biology,* John Wiley and Sons, Inc., NY, 1987.

In general, a DNA sequence encoding a zpep10 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zpep10 polypeptide into the secretory pathway of a host cell, a secretory signal sequence (also known as a signal sequence, leader sequence, prepro sequence or pre sequence) is provided in the expression vector. The secretory signal sequence may be that of the zpep10 polypeptide, or may be derived from another secreted protein (e.g., t-PA) or synthesized de novo. The secretory signal sequence is joined to the zpep10 DNA sequence in the correct reading frame and positioned to direct newly synthesized polypeptide into secretory pathways to host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues 1–20 of SEQ ID NO:2 is be operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology,* John Wiley and Sons, Inc., NY, 1987), liposome-mediated transfection (Hawley-Nelson et al., *Focus* 15:73, 1993; Ciccarone et al., *Focus* 15:80, 1993), and viral vectors (Miller and Rosman, *BioTechniques* 7:980–90, 1989; Wang and Finer, *Nature Med.* 2:714–16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S Pat. No. 4,656,134. Suitable cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S.

Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (angalore) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus; commonly derived from *Autographa californica* nuclear polyhedrosis virus (AcNPV). DNA encoding the zpep10 polypeptide is inserted into the baculoviral genome in place of the AcNPV polyhedrin gene coding sequence by one of two methods. The first is the traditional method of homologous DNA recombination between wild-type AcNPV and a transfer vector containing the zpep10 flanked by AcNPV sequences. Suitable insect cells, e.g. SF9 cells, are infected with wild-type AcNPV and transfected with a transfer vector comprising a zpep10 polynucleotide operably linked to an AcNPV polyhedrin gene promoter, terminator, and flanking sequences. See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and, Richardson, Ed., *Baculovirus Expression Protocols. Methods in Molecular Biology*, Totowa, N.J., Humana Press, 1995. Natural recombination within an insect cell will result in a recombinant baculovirus which contains zpep10 driven by the polyhedrin promoter. Recombinant viral stocks are made by methods commonly used in the art.

The second method of making recombinant baculovirus utilizes a transposon-based system described by Luckow et al. (*J. Virol.* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zpep10 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zpep10. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins and Possee, *J. Gen. Virol.* 71:971–6, 1990; Bonning et al., *J. Gen. Virol.* 75:1551–6, 1994; and, Chazenbalk and Rapoport, *J. Biol. Chem.* 270:1543–9, 1995. In such transfer vector constructs, a short or long version of the basic protein promoter can be used. Moreover, transfer vectors can be constructed which replace the native zpep10 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native secretory signal sequence. In addition, transfer vectors can include an in-frame fusion with DNA encoding an epitope tag at the C- or N-terminus of the expressed zpep10 polypeptide, for example, a Glu-Glu epitope tag (Grussenmeyer et al., ibid.) or FLAG tag (Kodak). Using a technique known in the art, a transfer vector containing zpep10 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zpep10 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat No. 5,300,435). Commercially available serum-free media are used to grow and maintain the cells. Suitable media are Sf900 II™ (Life Technologies) or ESF $_{921}$™ (Expression Systems) for the Sf9 cells; and Ex-cellO405™ (JRH Biosciences, Lenexa, Kans.) or Express FiveO™ (Life Technologies) for the T. ni cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. The recombinant virus-infected cells typically produce the recombinant zpep10 polypeptide at 12–72 hours post-infection and secrete it with varying efficiency into the medium. The culture is usually harvested 48 hours post-infection. Centrifugation is used to separate the cells from the medium (supernatant). The supernatant containing the zpep10 polypeptide is filtered through micropore filters, usually 0.45 μm pore size. Procedures used are generally described in available laboratory manuals (King and Possee, ibid.; O'Reilly et al., ibid.; Richardson, C. D., ibid.). Subsequent purification of the zpep10 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria Escherichia, Bacillus and other genera are also useful host cells within the present invention. Techniques for transforming these hosts and expressing foreign DNA sequences cloned therein are well known in the art (see, e.g., Sambrook et al., ibid.). When expressing a zpep10 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Zpep10 polypeptides or fragments thereof may also be prepared through chemical synthesis. Zpep10 polypeptides may be monomers or multimers; glycosylated or non-glycosylated; pegylated or non-pegylated; and may or may not include an initial methionine amino acid residue.

Expressed recombinant zpep10 polypeptides (or chimeric zpep10 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. DEAE Fast-Flow Sepharose (Pharmacia, Piscataway, N.J.), PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The zpep10 polypeptides of the present invention can be isolated by exploitation of their structural features. Within one embodiment of the invention are included a fusion of the polypeptide of interest and an affinity tag (e.g., polyhistidine, Glu—Glu, FLAG, maltose-binding protein, an immunoglobulin domain) that may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Proteins/polypeptides which bind zpep10 (such as a zpep10-binding receptor or other membrane glycoprotein) can also be used for purification of zpep10. The zpep10-binding protein/polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing zpep10 polypeptide are passed through the column one or more times to allow zpep10 polypeptide to bind to the ligand-binding or receptor polypeptide. The bound zpep10polypeptide is then eluted using changes in salt concentration, chaotropic agents (guanidine HCl), or pH to disrupt ligand-receptor binding.

In vitro and in vivo response to soluble zpep10 can also be measured using cultured cells or by administering molecules of the claimed invention to the appropriate animal model. For instance, soluble zpep10 transfected expression host cells may be embedded in an alginate environment and injected (implanted) into recipient animals. Alginate-poly-L-lysine micro-encapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

An alternative in vivo approach for assaying soluble proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161–89, 1994; and Douglas and Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection. Some disadvantages (especially for gene therapy) associated with adenovirus gene delivery include: (i) very low efficiency integration into the host genome; (ii) existence in primarily episomal form; and (iii) the host immune response to the administered virus, precluding readministration of the adenoviral vector.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. As used herein, the term complement/anti-complement pair denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

Zpep10 polypeptide and other ligand homologs can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–8, 1991; Cunningham et al., *Science* 245:821–5, 1991).

The invention also provides anti-zpep10 antibodies. Antibodies to zpep10 can be obtained, for example, using as an antigen the product of a zpep10 expression vector, or zpep10 isolated from a natural source. Particularly useful anti-zpep10 antibodies "bind specifically" with zpep10. Antibodies are considered to be specifically binding if the antibodies bind to a zpep10 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660, 1949). Suitable antibodies include antibodies that bind with zpep10, in particular the extracellular domain of zpep10 (amino acid residues 21–111 of SEQ ID NO:2).

Anti-zpep10 antibodies can be produced using antigenic zpep10 epitope-bearing peptides and polypeptides. Antigenic epitope-bearing peptides and polypeptides of the present invention contain a sequence of at least nine, preferably between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with zpep10. It is desirable that the amino acid sequence of the epitope-bearing peptide is selected to provide substantial solubility in aqueous solvents (i.e., the sequence includes relatively hydrophilic residues, while hydrophobic residues are preferably avoided). The hydrophobicity plot provided in the FIGURE provides such information. Using the plot antigenic regions can be selected, such as those found in the fragments, amino acid residue 39–44, 65–70, 38–43, 62–67 and 96–101 of SEQ ID NO:2. Moreover, amino acid sequences containing proline residues may be also be desirable for antibody production.

Polyclonal antibodies to recombinant zpep10protein or to zpep10 isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995). The immunogenicity of a zpep10 polypeptide can be increased through the use of an adjuvant, such as alum (aluminum hydroxide) or Freund's complete or incomplete adjuvant. Polypeptides useful for immunization also include fusion polypeptides, such as fusions of zpep10 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, hamsters, guinea pigs, goats or sheep, an anti-zpep10 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310, 1990. Antibodies can also be raised in transgenic animals such as transgenic sheep, cows, goats or pigs, and may be expressed in yeast and fungi in modified forms as will as in mammalian and insect cells.

Alternatively, monoclonal anti-zpep10antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1–2.6.7 (John Wiley & Sons 1991), Picksley et al., "Production of monoclonal antibodies against proteins expressed in *E. coli*," in *DNA Cloning 2*:

Expression Systems, *2nd Edition*, Glover et al. (eds.), page 93 (Oxford University Press 1995)).

Briefly, monoclonal antibodies can be obtained by injecting mice with a composition comprising a zpep10 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-zpep10 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nat. Genet.* 7:13, 1994, Lonberg et al., *Nature* 368:856, 1994, and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology*, Vol. 10, pages 79–104 (The Humana Press, Inc. 1992)).

For particular uses, it may be desirable to prepare fragments of anti-zpep10 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5 S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230, 1960, Porter, *Biochem. J.* 73:119, 1959, Edelman et al., in *Methods in Enzymology Vol.* 1, page 422 (Academic Press 1967), and by Coligan, ibid.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659, 1972. Alternatively, the variable chains can be linked by an intermolecular disulfide bond or cross-linked by chemicals such as gluteraldehyde (see, for example, Sandhu, *Crit. Rev. Biotech.* 12:437, 1992).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97, 1991, also see, Bird et al., *Science* 242:423, 1988, Ladner et al., U.S. Pat. No. 4,946,778, Pack et al., *Bio/Technology* 11:1271, 1993, and Sandhu, supra.

As an illustration, a scFV can be obtained by exposing lymphocytes to zpep10 polypeptide in vitro, and selecting antibody display libraries in phage or similar vectors (for instance, through use of immobilized or labeled zpep10 protein or peptide). Genes encoding polypeptides having potential zpep10 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zpep10 sequences disclosed herein to identify proteins which bind to zpep10.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-zpep10 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. USA* 86:3833, 1989. Techniques for producing humanized monoclonal antibodies are described, for example, by Jones et al., *Nature* 321:522, 1986, Carter et al., *Proc. Natl. Acad. Sci. USA* 89:4285, 1992, Sandhu, *Crit. Rev. Biotech.* 12:437, 1992, Singer et al., *J. Immun.* 150:2844, 1993, Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-zpep10 antibodies or antibody fragments, using standard techniques. See, for example, Green et al., "Production of Polyclonal Antisera," in *Methods In Molecular Biology: Immunochemical Protocols*, Manson (ed.), pages 1–12 (Humana Press 1992). Also, see Coligan, ibid. at pages 2.4.1–2.4.7. Alternatively, monoclonal anti-idiotype antibodies can be prepared using anti-zpep10 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875, 1996.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zpep10 polypeptides or anti-zpep10 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Soluble zpep10 polypeptides or antibodies to zpep10 can be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zpep10 polypeptides or anti-zpep10 antibodies, or bioactive fragments or portions thereof, can be coupled to detectable or cytotoxic molecules and delivered to a mammal having cells, tissues or organs that express the anti-complementary molecule.

Suitable detectable molecules can be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules can be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies can also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Such polypeptide-toxin fusion proteins or antibody/fragment-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain can be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates. The bioactive polypeptide or antibody conjugates described herein can be delivered intravenously, intraarterially or intraductally, or may be introduced locally at the intended site of action.

The zpep10 gene is almost exclusively expressed in the testis. Low levels of transcript are also seen in a number of other tissues, with the kidney accounting for most of the ancillary expression. The tissue specificity observed for zpep10 suggests a general role in development and regulatory control of testicular differentiation and gonadal steroidogenesis and spermatogenesis. Zpep10 polypeptides, agonists and antagonists have enormous potential in both in vitro and in vivo applications.

Development of testicular hormone production can be divided into early and late steps, with the latter dependent on the activation of functionally-determined Leydig cell precursors by LH. However, the factors that control the early steps in this process remain unknown (Huhtaniemi, *Reprod. Fertil. Dev.* 7: 1025–35, 1995) suggesting that testis specific polypeptides such as zpep10 might be responsible for activation of a non-steroidogenic, non-LH responsive precursor cell.

Once Leydig cell differentiation has occurred, production of steroid hormones in the testis is dependent on the secretion of the gonadotrophins, LH and FSH, by the pituitary. LH stimulates production of testosterone by the Leydig cells, whereas spermatogenesis depends on both FSH and high intratesticular testosterone concentrations. LH and FSH secretion is in turn under control of gonadotrophin releasing hormone (GnRH) produced in the hypothalamus (Kaufman, *The neuro endocrine regulation of male reproduction*. in: Male Infertility. Clinical Investigation, Cause Evaluation and Treatment., F H Comhaire, ed., Chapman and Hall, London, pp 29–54, 1996). Since testicular products have been shown to control LH and FSH production and in turn, these products regulate, testicular function, this suggests a regulatory role for zpep10 in hormone production by the hypothalamic, pituitary, gonadal axis.

It is well known that steroidogenesis and spermatogenesis take place within two different cellular compartments of the testes, with Leydig and Sertoli cells responsible for the former and latter, respectively (Saez, *Endocrin. Rev.* 15: 574–626, 1994). The activity of each of these cell types appears to be regulated by the secretory products of the other. Sertoli cell derived tumor necrosis factor-a, fibroblast growth factor, interleukin-1 transforming growth factor-β, epidermal growth factor/transforming growth factor-α, activin, inhibin, insulin-like growth factor-1, platelet derived growth factor, endothelin, and ariginine-vasopressin have all been shown to regulate Leydig cell function (Saez, *Endocrin. Rev.* 15: 574–626, 1994). Thus, zpep10 might control or modulate the activities of one or more of these genes.

The membrane glycoprotein zpep10 may also function as a binding site for one or more growth factor peptides or hormones in much the same way that heparin binds with platelet-derived growth factor (PDGF), fibroblast growth factors (such as aFGF and bFGF) and vascular endothelial growth factor (VFGF) and sequesters them on the cell surface.

In men, aging is associated with a progressive decline in testicular function. These changes are manifest clinically by decreased virility, vigor, and libido that point towards a relative testicular deficiency (Vermeulen, *Ann. Med.* 25:531–4, 1993; Pugeat et al., *Horm. Res.* 43: 104–10, 1995). Hormone replacement therapy in elderly men is not currently recommended which suggests that a new therapy for the male climacterium would be very valuable. Zpep10 polypeptides, agonists or antagonists, either independently or in combination with other factors, may be evaluated therapeutically.

Soluble zpep10 polypeptides, zpep10 agonists and/or zpep10 antagonists may also have therapeutic value in treatment of testicular cancer, infertility, or in the recovery of function following testicular surgery.

The ability of zpep10 polypeptides and zpep10 agonists to stimulate proliferation or differentiation of testicular cells can be measured using cultured testicular cells or in vivo by administering molecules of the present invention to the appropriate animal model. Cultured testicular cells include dolphin DB1.Tes cells (CRL-6258); mouse GC-1 spg cells (CRL-2053); TM3 cells (CRL-1714); TM4 cells (CRL-1715); and pig ST cells (CRL-1746), available from American Type Culture Collection, 10801 University Boulevard, Manassas, Va. Assays measuring cell proliferation or differentiation are well known in the art. For example, assays measuring proliferation include such assays as chemosensitivity to neutral red dye (Cavanaugh et al., *Investigational New Drugs* 8:347–354, 1990, incorporation of radiolabelled nucleotides (Cook et al., *Anal. Biochem.* 179:1–7, 1989), incorporation of 5-bromo-2'-deoxyuridine (BrdU) in the DNA of proliferating cells (Porstmann et al., *J. Immunol. Methods* 82:169–79, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–33, 1988) and by measuring proliferation using $^3$H-thymidine uptake (Crowley et al., *J. Immunol. Meth.* 133:55–66, 1990). Assays measuring differentiation include, for example, measuring cell-surface markers associated with stage-specific expression of a tissue, enzymatic activity, functional activity or morphological changes (Watt, *FASEB*, 5:281–4, 1991; Francis, *Differentiation* 57:63–75, 1994; Raes, *Adv. Anim. Cell Biol. Technol. Bioprocesses*, 161–71, 1989).

Zpep10 polypeptides, agonists and antagonists will also prove useful in the study of spermatogenesis and infertility. In vivo, zpep10 agonists may find application in the treatment of male infertility. Zpep10 antagonists may be useful as male contraceptive agents. Zpep10 antagonists are useful as research reagents for characterizing sites of ligand-receptor interaction.

In vivo assays, well known in the art, are available for evaluating the effect of zpep10 ligands and agonists on testes. For example, compounds can be injected intraperitoneally for a specific time duration. After the treatment period, animals are sacrificed and testes removed and weighed. Testicles are homogenized and sperm head counts are made (Meistrich et al., *Exp. Cell Res.* 99:72–8, 1976). Other activities, for example, chemotaxic activity that may be associated with proteins of the present invention can be analyzed. For example, late stage factors in spermatogenesis are involved in egg-sperm interactions and sperm motility. Activities, such as enhancing viability of cryopreserved sperm, stimulating the acrosome reaction, enhancing sperm motility and enhancing egg-sperm interactions may be associated with the ligands and agonists of the present invention. Assays evaluating such activities are known (Rosenberger, *J. Androl.* 11:89–96, 1990; Fuchs, *Zentralbl. Gynakol.* 11:117–120, 1993; Neurwinger et al., *Andrologia* 22:335–9, 1990; Harris et al., *Human Reprod.* 3:856–60, 1988; and Jockenhovel, *Andrologia* 22:171–178, 1990; Lessing et al., *Fertil. Steril.* 44:406–9, 1985; Zaneveld, In Male Infertility Chapter 11, Comhaire Ed., Chapman & Hall, London 1996). These activities are expected to result in enhanced fertility and successful reproduction.

Localization of zpep10 to testis tissue suggests zpep10, its agonists and/or antagonists may have applications in enhancing fertilization during assisted reproduction in humans and in animals. Such assisted reproduction methods are known in the art and include artificial insemination, in vitro fertilization, embryo transfer and gamete intrafallopian transfer. Such methods are useful for assisting men and women who may have physiological or metabolic disorders that prevent natural conception. Such methods are also used in animal breeding programs, such as for livestock, zoological animals, endangered species or racehorses and could be used as methods for the creation of transgenic animals.

To verify the presence of this capability in zpep10 polypeptides, agonists or antagonists of the present invention, such molecules are evaluated with respect to their ability to enhance viability of cryopreserved sperm, sperm motility, the ability of sperm to penetrate cervical mucus, particularly in association with methods of assisted reproduction, according to procedures known in the art (see for example, Juang et al., *Anim. Reprod. Sci.* 20:21–9, 1989; Juang et al., *Anim. Reprod. Sci.* 22:47–53, 1990; Colon et al.,

*Fertil. Steril.* 46:1133–39, 1986; Lessing et al., *Fertil. Steril.* 44:406–9, 1985 and Brenner et al., *Fertil. Steril.* 42:92–6, 1984). If desired, zpep10 polypeptide performance in this regard can be compared to relaxins and the like. In addition, zpep10 polypeptides or agonists or antagonists thereof may be evaluated in combination with one or more proteins to identify synergistic effects. For example, soluble zpep10, agonists and/or antagonists can be added to "capacitation media", a cocktail of compounds known to activate sperm, such as caffeine, dibutyl cyclic adenosine monophosphate (dbcAMP) or theophylline. Such mixtures have resulted in improved reproductive function of the sperm, in particular, sperm motility and zonae penetration (Park et al., *Am. J. Obstet. Gynecol.* 158:974–9, 1988; Vandevoort et al., *Mol. Repro. Develop.* 37:299–304, 1993; Vandevoort and Overstreet, *J. Androl.* 16:327–33, 1995). The capacitation mixture can then be combined with sperm, an egg or an egg-sperm mixture prior to fertilization of the egg.

In cases where pregnancy is not desired, zpep10polypeptides or polypeptide fragments may function as germ-cell-specific antigens for use as components in "immunocontraceptive" or "anti-fertility" vaccines to induce formation of antibodies and/or cell mediated immunity to selectively inhibit a process, or processes, critical to successful reproduction in humans and animals. The use of sperm and testis antigens in the development of an immunocontraceptive have been described (O'Hern et al., *Biol Reprod.* 52:311–39, 1995; Diekman and Herr, *Am. J. Reprod. Immunol.* 37:111–17, 1997; Zhu and Naz, *Proc. Natl. Acad. Sci. USA* 94:4704–9,1997). A vaccine based on human chorionic gonadotrophin (HCG) linked to a diphtheria or tetanus carrier is currently in clinical trials (Talwar et al., *Proc. Natl. Acad. Sci. USA* 91:8532–36, 1994). A single injection resulted in production of high titer antibodies that persisted for nearly a year in rabbits (Stevens, *Am. J. Reprod. Immunol.* 29:176–88, 1993). Such methods of immunocontraception using vaccines would include a zpep10 testes-specific protein or fragment thereof. The zpep10 protein or fragments can be conjugated to a carrier protein or peptide, such as tetanus or diphtheria toxoid. An adjuvant, as described above, can be included and the protein or fragment can be noncovalently associated with other molecules to enhance intrinsic immunoreactivity. Methods for administration and methods for determining the number of administrations are known in the art. Such a method might include a number of primary injections over several weeks followed by booster injections as needed to maintain a suitable antibody titer.

For pharmaceutical use, pharmaceutically effective amounts of zpep10 therapeutic antibodies, small molecule antagonists or agonists of zpep10 polypeptides, or zpep10 polypeptide fragments or soluble zpep10 receptors can be formulated with pharmaceutically acceptable carriers for parenteral, oral, nasal, rectal, topical, transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of the zpep10 polypeptide, agonist or antagonist. Such slow release systems are applicable to formulations, for example, for oral, topical and parenteral use. The term "pharmaceutically acceptable carrier or vehicle" refers to a carrier medium which does not interfere with the effectiveness of the biological activity of the active ingredients and which is not toxic to the host or patient. One skilled in the art may formulate the compounds of the present invention in an appropriate manner, and in accordance with accepted practices, such as those disclosed in Remington: *The Science and Practice of Pharmacy*, Gennaro, ed., Mack Publishing Co., Easton, Pa., 19th ed., 1995.

As used herein, a pharmaceutically effective amount of a zpep10 polypeptide, agonist or antagonist, is an amount sufficient to induce a desired biological result. The result can be alleviation of the signs, symptoms, or causes of a disease, or any other desired alteration of a biological system. For example, an effective amount of a polypeptide of the present invention is that which provides either subjective relief of symptoms or an objectively identifiable improvement as noted by the clinician or other qualified observer. Doses of zpep10 polypeptide will generally be determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows the designing of PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR based, chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The present invention provides reagents for use in diagnostic applications. For example, the zpep10 gene, a probe comprising zpep10 DNA or RNA, or a subsequence thereof can be used to determine if the zpep10 gene is present on a particular chromosome or if a mutation has occurred. Detectable chromosomal aberrations at the zpep10 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, PCR Methods and Applications 1:34–8, 1991).

Polynucleotides encoding zpep10 polypeptides are useful within gene therapy applications where it is desired to increase or inhibit zpep10 activity. If a mammal has a mutated or absent zpep10 gene, the zpep10 gene can be introduced into the cells of the mammal. In one embodiment, a gene encoding a zpep10 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zpep10 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zpep10 gene translation, such as to inhibit cell proliferation in vivo. Polynucleotides that are complementary to a segment of a zpep10-encoding polynucleotide (e.g., a polynucleotide as set froth in SEQ ID NO:1) are designed to bind to zpep10-encoding mRNA and to inhibit translation of such mRNA. Such antisense polynucleotides are used to inhibit expression of zpep10 polypeptide-encoding genes in cell culture or in a subject.

Transgenic mice, engineered to express the zpep10 gene, and mice that exhibit a complete absence of zpep10 gene function, referred to as "knockout mice" (Snouwaert et al., *Science* 257:1083, 1992), may also be generated (Lowell et al., *Nature* 366:740–42, 1993). These mice may be employed to study the zpep10 gene and the protein encoded thereby in an in vivo system.

The invention is further illustrated by the following non-limiting examples.

EXAMPLES

Example 1

Identification of Zpep10

The zpep10 polypeptide-encoding polynucleotides of the present invention were initially identified by querying an EST database for polypeptides containing repetitive patterns and post-translational processing sites yielding potentially active peptides. The polypeptide encoded by an EST meeting those search criteria was further analyzed and found to be a membrane glycoprotein. The EST sequence was from a testis cell library. Several clones considered likely to contain the entire coding region were used for sequencing and resulted in incompletely spliced messages. A minimal nucleotide sequence having all potential introns spliced out was generated from these sequences.

To obtain the complete cDNA sequence a human testis library was screened. The library was plated in pools of 12,000. Plasmid DNA was prepared from the plated bacteria using a Qiagen® plasmid purification column (Qiagen, Inc., Chatsworth, Calif.) according to the manufacturer's instructions. DNA from these pools were used as template DNA to identify pools containing the DNA encoding zpep10 using PCR. Oligonucleotide primers ZC16,186, (SEQ ID NO:9) and ZC16,187, (SEQ ID NO:10) were designed from the sequence of the EST. One nanogram of template DNA was combined with 20 pmoles of each primer in a PCR mixture. The reaction mixture was incubated at 94° C. for 5 minutes, then run for 35 cycles of 94° C., 30 seconds and 68° C., 30 seconds; followed by an extension at 68° C. for 7 minutes. Pools having the correct sized PCR produce, 290 bp, were used as a template for PCR isolation of the 5' end of the clones. Sequence specific primer ZC16,186 (SEQ ID NO:9) and vector specific primer ZC13,006 (SEQ ID NO:11) were used in PCR reactions as above. PCR products were purified by Qiaex II Gel Extraction Kit (Qiagen, Inc.) according to manufacturer's instructions and sequenced. Pools which contained the clones with the most fully spliced sequence were used to transform *E. coli* and plated to agar. The colonies were transferred to nitrocellulose and probed with a 290 bp fragment derived above. The probe was radioactively labeled using the MULTIPRIME DNA labeling kit (Amersham, Arlington Heights, Ill.) according to the manufacturer's instructions. The probe was purified using a NUCTRAP push column (Stratagene). ExpressHyb (Clontech) solution was used for prehybridization and as a hybridizing solution for the colony lifts. Hybridization took place at 65° C. for over 12 hours using 1.2×10$^6$ cpm/ml of labeled probe. The filters were then washed 4 times at 5 minutes each in 2× SSC, 0.005% SDS at 25° C. followed by 2 washes at 20 minutes each in 0.1× SSC, 0.1% SDS at 50° C. with continuous agitation. Plasmid DNA from those colonies producing a signal were isolated and sequenced. The 1094 bp (SEQ ID NO:1) sequence encoding the a full length zpep10polypeptide was isolated. An intron may be contained within the 3' untranslated region from base pairs 560–784 of SEQ ID NO:1.

Example 2

Tissue Distribution

Human Multiple Tissue Northern Blots (MTN I, MTN II and MTN III; Clontech) were probed to determine the tissue distribution of human zpep10 expression. An approximately 530 bp probe, entirely 3' UTR was derived by restriction digest of the clone described above with Not I and Eco RI. The restriction digested fragment was visualized by agarose gel electrophoresis and purified using Qiaex II (Qiagen, Chatsworth, Calif.) according to manufacturer's instructions. The probe was radioactively labeled using the MULTIPRIME DNA labeling kit (Amersham, Arlington Heights, Ill.) according to the manufacturer's instructions. The probe was purified using a NUCTRAP push column (Stratagene) EXPRESSHYB (Clontech) solution was used for prehybridization and as a hybridizing solution for the Northern blots. Hybridization took place overnight at 65° C. using and the blots were then washed at 50° C. in 1× SSC, 0.1% SDS. A 1.5 kb transcript corresponding to zpep10 was seen in testis and a non-discrete smear was seen in kidney.

A RNA Master Dot Blot (Clontech) that contained RNAs from various tissues that were normalized to 8 housekeeping genes was also probed and hybridized as described above. The highest level of expression was seen in testis with significantly reduced expression in kidney.

What is claimed is:

1. An isolated polypeptide comprising an extracellular domain, wherein said extracellular domain comprises amino acid residues 22 to 111 of the amino acid sequence of SEQ ID NO:2.

2. An isolated polypeptide according to claim 1, wherein said polypeptide further comprises a transmembrane domain that resides in a carboxyl-terminal position relative to said extracellular domain, wherein said transmembrane domain comprises amino acid residues 112 to 133 of the amino acid sequence of SEQ ID NO:2.

3. An isolated polypeptide according to claim 2, wherein said polypeptide further comprises a cytoplasmic domain that resides in a carboxyl-terminal position relative to said transmembrane domain, wherein said cytoplasmic domain comprises amino acid residues 134 to 142 of the amino acid sequence of SEQ ID NO:2.

4. An isolated polypeptide according to claim 2, wherein said polypeptide further comprises a secretory signal that resides in an amino-terminal position relative to said extracellular domain, wherein said secretory signal sequence comprises amino acid residues 1 to 20 of the amino acid sequence of SEQ ID NO:2.

5. An isolated polypeptide according to claim 1 comprising amino acid residue 1 to amino acid residue 142 of SEQ ID NO:2.

6. An isolated polypeptide according to claim 1, covalently linked amino terminally or carboxy terminally to a moiety selected from the group consisting of affinity tags, toxins, radionucleotides, enzymes and fluorophores.

7. An isolated polypeptide comprising a sequence of amino acid residues that is at least 80% identical to a amino acid residue 21 to amino acid residue 142 of SEQ ID NO:2, wherein said polypeptide specifically binds with an antibody that specifically binds with a polypeptide having the amino acid sequence of SEQ ID NO:2.

8. An isolated polypeptide according to claim 7, wherein any difference between said amino acid sequence of said isolated polypeptide and said corresponding amino acid sequence of SEQ ID NO:2 is due to a conservative amino acid substitution.

9. An isolated polypeptide of claim 7, wherein the amino acid percent identity is determined using a FASTA program with ktup=1, gap opening penalty=10, gap extension penalty=1, and substitution matrix=blosum62, with other parameters set as default.

10. An isolated polypeptide comprising the amino acid sequence of amino acid residue 1 to amino acid residue 20 of SEQ ID NO:2.

11. An isolated polypeptide selected from the group consisting of:
  a) amino acid residues 21–111 of SEQ ID NO:2;
  b) amino acid residues 112–133 of SEQ ID NO:2;
  c) amino acid residues 134–142 of SEQ ID NO:2;
  d) amino acid residues 1–20 of SEQ ID NO:2;
  e) amino acid residues 21–133 of SEQ ID NO:2;
  f) amino acid residues 112–142 of SEQ ID NO:2;
  g) amino acid residues 1–111 of SEQ ID NO:2; and
  h) amino acid residues 1–133 of SEQ ID NO:2.

12. A fusion protein consisting of a first portion and a second portion joined by a peptide bond, said first portion comprising a polypeptide according to claim 1, and said second portion comprising another polypeptide.

13. A polypeptide according to claim 1 in combination with a pharmaceutically acceptable vehicle.

* * * * *